United States Patent
Bargiacchi et al.

(10) Patent No.: US 8,536,090 B2
(45) Date of Patent: Sep. 17, 2013

(54) USE OF NATURAL EXTRACTS OF TANNIN AND NON-TANNIN MATERIALS FOR IMPROVING SOIL FERTILITY AND PROVIDING A STARTER EFFECT ON CULTIVATIONS, AND A TANNIN AND NON-TANNIN PHYTOCOMPOSITION THEREFOR

(75) Inventors: Enrica Bargiacchi, Siena (IT); Gianluca Costa, Siena (IT); Sergio Miele, Siena (IT); Simone Magni, Siena (IT)

(73) Assignee: Gruppo Mauro Saviola S.R.L., Viadana (MN) (IT)

(*) Notice: Subject to any disclaimer, the term of this patent is extended or adjusted under 35 U.S.C. 154(b) by 263 days.

(21) Appl. No.: 12/930,609

(22) Filed: Jan. 11, 2011

(65) Prior Publication Data
US 2011/0174031 A1 Jul. 21, 2011

(30) Foreign Application Priority Data
Jan. 15, 2010 (IT) .............................. MI2010A0040

(51) Int. Cl.
*C05F 11/00* (2006.01)

(52) U.S. Cl.
USPC ............... 504/100; 47/1.01 R; 47/57.6; 71/23

(58) Field of Classification Search
USPC .................. 71/11–63; 504/100; 47/58.1 SE, 47/1.01 R, 57.6
See application file for complete search history.

(56) References Cited

U.S. PATENT DOCUMENTS

| 8,375,629 B2* | 2/2013 | Prasad | 47/57.6 |
| 2002/0050096 A1* | 5/2002 | Bonfiglio | 47/57.6 |
| 2010/0058822 A1* | 3/2010 | Bargiacchi | 71/17 |
| 2012/0157304 A1* | 6/2012 | Johnson | 504/100 |

* cited by examiner

*Primary Examiner* — Wayne Langel
(74) *Attorney, Agent, or Firm* — Hedman & Costigan, P.C.; James V. Costigan; Kathleen A. Costigan

(57) ABSTRACT

A use of a tannin and non tannin material phytocomposition or phytocomplex, either in a dry or liquid form, applied to the seedling seeds or seedling agamic multiplication members, or to implanted seedlings, to promote the starter effect, i.e. strong stimulation of the seedling initial growth. The phytocomposition is made by leaching a biomass of one or more of the following species: *Castanea* spp., *Juglans* spp., *Eucalyptus* spp., *Quercus* spp., *Salix* spp., *Vitis* spp., *Mimosa* ssp., *Schinopsis* spp., *Olea europaea*, *Onobrychis viciifolia*, *Rhamnus* spp., *Artemisia* spp., *Lawsonia inermis*, either in a single form or in a mixture in all mixing ratios.

6 Claims, 1 Drawing Sheet

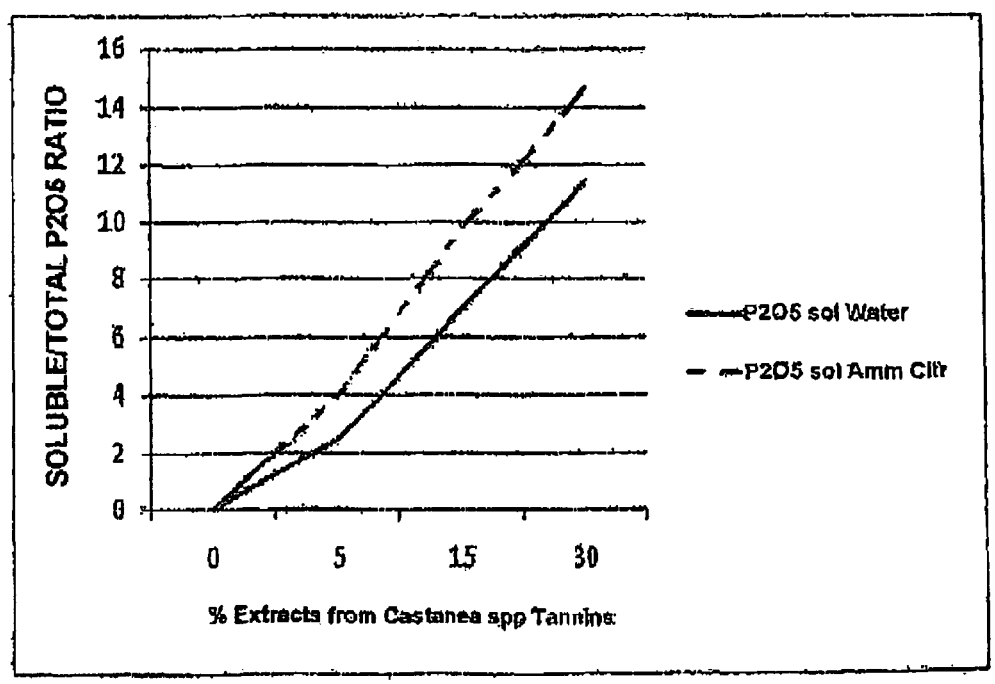

USE OF NATURAL EXTRACTS OF TANNIN AND NON-TANNIN MATERIALS FOR IMPROVING SOIL FERTILITY AND PROVIDING A STARTER EFFECT ON CULTIVATIONS, AND A TANNIN AND NON-TANNIN PHYTOCOMPOSITION THEREFOR

BACKGROUND OF THE INVENTION

The present invention relates to a use of natural extracts of tannin and non-tannin materials for improving soil fertility and providing a starter effect on cultivations, and a tannin and non-tannin phytocomposition or phytocomplex therefor.

In the present invention, for "tannin and non-tannin phytocomposition or phytocomplex" it is intended an aqueous extract of a vegetable biomass of suitable plants.

The present invention is related to the agriculture field and, in particular, to improving the soil fertility and cultivation starter effect.

By "starter effect" it is herein intended a stimulation to the growth of a young seedling, born from a seedling seed, or put in place or implanted by a transplantation operation, to allow the seedling to growth in a time as short as possible, and to achieve a comparatively high cultivation yield, owing to a better exploitation of an environmental availability and growth seasons and a more active response to adverse conditions.

As is known, the starter effect is related to the increase of the availability of nutritional elements adapted to be quickly assimilated or absorbed, and a consequent physiologic induction of the plant or seedling growth even under comparatively low temperature and poor soil fertility conditions.

In fact, in many cases, soil physical-chemical and biologic conditions may cause a reduction of the seedling growth and root absorbing activity, as well as of the solubility of phosphoric anhydride and a number of microelements which are present in the soil either naturally or which have been pre-added during soil manuring operations.

Thus, a correction of soil negative characteristics near the plants may positively affect the nutritional element recovery, with important advantages from the agronomic (an improved efficiency of the manuring elements being applied), economic (a less manuring cost) and ecologic (an excess manuring to balance insolubilization phenomena related to the soil effect would increase a pollution risk because of an environmental nutritional element dispersion) standpoints.

The European patent application EP-1 464 635 discloses a method for making salinity adjusting and acidifying organic solutions, and nitrogen and/or microelement based fertilizers, prepared starting from tannin and non-tannin material rich vegetable extracts.

The European patent application EP-1 097 912 discloses an organic-mineral manure for biologic agriculture based on a natural phosphorite, blood and tannins.

SUMMARY OF THE INVENTION

Thus, the aim of the present invention is to overcome the above disclosed prior art drawbacks.

Within the above aim, a main object of the invention is to overcome the need of a pre-preparing manures including tannin and non-tannin material phytocomposition.

Another object of the present invention is to eliminate the need of applying solutions of the above products to the soil.

According to one aspect of the present invention, the above aim and objects, as well as yet other objects, which will become more apparent hereinafter, are achieved by a use of a tannin and non-tannin materials phytocomposition, either in a dry or liquid form, to be applied to seedling seeds of agamic multiplication members, or to implanted seedlings, to promote the starter effect, i.e. a strong stimulation of the seedling initial growth.

The above mentioned aim and objects, as well as yet other objects which will become more apparent hereinafter, are further achieved by a tannin and non-tannin material phytocomposition to promote the starter effect, that is a strong stimulation to an initial growth, in seeds or agamic multiplication members, or in implanted seedlings, characterized in that said phytocomposition is made by leaching the biomass of one or more of the following species: *Castanea* spp., *Juglans* spp., *Eucalyptus* spp., *Quercus* spp., *Salix* spp., *Vitis* spp., *Mimosa* ssp., *Schinopsis* spp., *Olea europaea*, *Onobrychis viciifolia*, *Rhamnus* spp., *Artemisia* spp., *Lawsonia inermis*, either in a single form or in a mixture in all mixing ratios.

BRIEF DESCRIPTION OF THE DRAWING

Further characteristics and advantages of the present invention will become more apparent from the following detailed disclosure of preferred, though not exclusive, embodiments of the invention, which are illustrated, by way of an indicative but not limitative example, in the accompanying drawing, where:

The drawing shows a diagram illustrating the evolvement of a ratio of water soluble $P_2O_5$ and neutral ammonium citrate and total $P_2O_5$ upon processing a tricalcium phosphate material by a phytocomposition according to the present invention.

DESCRIPTION OF PREFERRED EMBODIMENTS

More specifically, the invention provides to apply, either in a liquid (solution or suspension) or a solid (powder, pellet or granule) form of a tannin and non-tannin phytocomposition or phytocomplex, made by water leaching a vegetable biomass and, in particular, a woody biomass, and by concentrating the obtained extract by physical methods.

Unexpectedly, the tannin and non-tannin material phytocomposition, applied at comparatively low doses (1-1000 kg/he and, in particular, 5-250 kg/he dry phytocomposition) and preferably in a localized manner to the seedling or seed, has been found to greatly improve the growth rate of plants and seedlings from seeds and agamic multiplication members, or from transplanted seedlings.

The tannin and non-tannin material phytocomposition according to the present invention is preferably applied either before or during the cultivation sowing or transplanting operations, both along and under said row, or it may be evenly distributed on a soil strip bridging the sowing or transplanting row, to maximize the product bioagronomic effect on the rhizosphere of the plant being processed.

If a micro-irrigation or a localized irrigation system is provided, then said phytocomposition may also be applied with the irrigation water, preferably in the first processing operations; this mode of operation would be also suitable in a case of arborious and vessel growing cultivations.

In a case of plants which are not sown or transplanted in rows, the tannin and non-tannin phytocomposition may also be mixed to the seed or agamic multiplication members (rhizomes, bulbs, bulbils and so on), both as a dry powder and in a moist or slurry form, in suitable concentrations, according to the so-called "tanning" process.

In a case of plants the seeds of which are "candied", that is coated by a composite material, so to make the seed size even and provide the seed with an even spherical shape, and to allow it to be easily deposited on the soil by pneumatic or mechanical sowing machines, the phytocomposition may finally be used in formulating coating materials, the so-called "compounds".

The coated seed, which opens at a germination time, will convey, in a localized manner, at a level of the seed depositing micrositus, the tannin and non-tannin phytocomposition according to the present invention.

For better understanding the invention, several non limitative examples thereof will be hereinbelow disclosed, which do not intend to limit the invention scope as defined in the accompanying claims.

Example 1

The phytocomposition according to the present invention has been applied, in a farm test procedure, and in liquid form and a "low" dose (100 l/he in pre-implantation+3×10 l/he in tert-irrigation in post-implantation) as well as a "high" dose (140 l/he in pre-implantation+3×20 l/he in tert-irrigation in post-implantation) on lettuce cultivated on an artificially pre-salted soil at 3.5 and 5 dS/cm.

The comparison has been made by an unprocessed sample and a suitable anti-salinity product.

Both at average and high salinity, the phytocomposition "low" dose provided a larger fresh and dry substance yield, with a yield increase of 45.8% with respect to the anti-salinity product and larger than 100% with respect to the sample or specimen.

Example 2

A tannin and non-tannin material phytocomposition according to the invention in a dose of about 75 l/he product with a 13% w/w tannin amount has been applied by a sleeve irrigation method on a conventional kneaded or mixed soil.

Upon analyzing the soil at the wet area thereof, an increase of the absorption of some nutritional elements, very important for the plants, and, in particular phosphorus, potassium, calcium, sulphur, boron, iron, copper, manganese and zinc has been found.

Example 3

30 l of a phytocomposition according to the present invention, for each $m^3$ of water distributed through a localized micro-irrigation have been added to tobacco leaves by three irrigation operations carried out in a time period from 40 to 80 days from transplantation.

Upon processing, the tobacco plants anticipated their blooming by about a week, with an increase of the tobacco leaves of 3% and of about 1.5 evaluation points (on a scale of 10) related to the evaluation examination.

In the tobacco leaves, reducing sugars increased by 2 rate units, and remarkable increases of nicotine, phosphorus and potassium rates have been achieved.

Example 4

To evaluate the effect of the inventive phytocomposition on the absorption of phosphoric anhydride present in soil in the form of tricalcium anhydride, sedimentary tricalcium phosphate, with a total $P_2O_5$ rate or amount of 30-32% by weight, alkaline and calcareous soils, such as those typical of South-Europe and Italy in particular, have been experimentally tested.

The test comprised a treatment of the tricalcium 2U phosphate (100 g) with 180 ml of a solution containing different concentrations of a liquid form phytocomposition (at 13% w/w tannins) followed by mixing and air drying steps. The results have been evaluated after a week from the treatment.

In particular, values of pH and water soluble $P_2O_5$ and neutral ammonium citrate, according to Official National measurement methods with respect to the extracting step, but not with respect to the determining step have been measured.

In this test procedure, the Dionex ionic chromatography, (instead of spectrophotometry), for preventing interactions with tannin colors, has been used.

The results are shown in the following Table 1.

TABLE 1 effect of an addition of phytocomposition solutions at different concentrations on pH and tricalcium phosphate absorption.

| TRICALCIUM PHOSPHATE % w/w | TANNIN AND NON-TANNIN PHYTO-COMPOSITION % | pH | WATER SOLUBLE $P_2O_5$ % on t.q. | AMMONIUM CITRATE SOLUBLE $P_2O_5$ % on t.q. |
|---|---|---|---|---|
| 100 | 0 | 8.51 | n.r. | n.r. |
| 95 | 5 | 7.38 | 0.76 | 1.21 |
| 85 | 15 | 6.71 | 1.88 | 2.65 |
| 70 | 30 | 6.12 | 2.54 | 3.27 | n.r.=less than the method detection limits (0.01%)

From the above data it is possible to see that the effect of the inventive phytocomposition on the tricalcium phosphate pH is very remarkable, it being associated with a progressive increase of the water soluble phosphoric anhydride and neutral ammonium citrate rate or amount. In particular, as the is phytocomposition concentration increases, the water soluble phosphoric anhydride and citrate amount varies from 0 to about 12% of the total tricalcium phosphate contents (see FIG. 1).

FIG. 1—A variation of the ratio of water soluble $P_2O_5$ and neutral ammonium citrate and total $P_2O_5$ upon processing the tricalcium phosphate by the inventive phytocomposition.

The above result is very interesting with respect to alkaline and calcareous grown cultivations, which tend to quickly retrograde phosphoric anhydride applied by manure. Thus, it is possible to properly exploit phosphorus amounts which could not be previously absorbed.

Example 5

Extensive studies are being performed on to germination and first growth of caryopses and seeds of: wheat, maize, soybean, alfalfa and potato tubers, processed by the following pre-treatments by the inventive phytocomposition in a powder form: 1) water dispersions at concentrations of 1%, 5% and 10% and then by spraying the seeds/tubers before "sowing" (the sprayed liquid amount being yet to be defined); 2) a dry tanning of the seeds/tubers at concentrations of 1%, 2.5%, 5%, 7.5%, 10% by weight of the treated seeds/tubers (where 100 is the amount of seeds/tubers which are normally used per, hectare).

Example 6

At present are being performed studies on introducing the compound used for coating the tobacco seed and concentration core of the inventive tannin and non-tannin phytocomposition corresponding to a 1.5 and 10% amount by weight.

It has been found that the invention fully achieves the intended aim and objects.

The invention claimed is:

1. A dry or liquid phytocomposition of tannin and non-tannin materials to be applied to seeds or agamic multiplication members, or to implanted seedlings, to promote the starter effect consisting of a strong stimulation of an initial growth thereof, said phytocomposition comprising a water leached biomass of at least a plant species selected from the group consisting of *Castanea* spp., *Juglans* spp., *Eucalyptus* spp., *Quercus* spp., *Salix* spp., *Vitis* spp., *Mimosa* spp., *Schinopsis* spp., *Olea europaea, Onobrychis viciifolia, Rhamnus* spp., *Artemisia* spp., *Lawsonia inermis*, and mixtures thereof.

2. A method for pre-sowing/pre-transplanting localization, sowing/transplanting localization, post-sowing/transplanting localization, a pre- and post-implantation localization irrigation and seed/agamic multiplication member tanning, of seeds, agamic multiplication members or implanted seedings, said method comprising coating said seeds, agamic multiplication members or implanted seedling with or mixing in a cultivation substrate or in vessels for growing transplanted plants, a phytocomposition according to claim 1.

3. A phytocomposition, according to claim 1, characterized in that said phytocomposition is capable of increasing an absorption of nutritional elements present in a cultivation soil or medium.

4. A phytocomposition according to claim 1, characterized in that said phytocomposition is capable of increasing a recovery by a plant of nutritional elements present in a cultivation soil or medium.

5. A method according to claim 2, characterized in that said phytocomposition is applied to a cultivation soil or medium having a water pH larger than 6.5.

6. A method according to claim 2, characterized in that said method comprises a step of applying said photocomposition at a dose from 5 to 250 kg/he of said phytocomposition in a dry form thereof.

* * * * *